United States Patent [19]

Yano

[11] Patent Number: 5,701,197
[45] Date of Patent: Dec. 23, 1997

[54] SLIT LAMP MICROSCOPE PROVIDED WITH A CONFOCAL SCANNING MECHANISM

[75] Inventor: Nobuyuki Yano, Okazaki, Japan

[73] Assignee: Nidek Co., Ltd., Japan

[21] Appl. No.: 545,900

[22] Filed: Oct. 20, 1995

[30] Foreign Application Priority Data

Nov. 8, 1994 [JP] Japan .................. 6-300395

[51] Int. Cl.$^6$ .................. G02B 21/06; G02B 21/00
[52] U.S. Cl. .................. 359/389; 359/368; 359/385; 359/227; 351/214
[58] Field of Search .................. 359/368, 385, 359/381, 384, 388, 389; 351/206, 208, 243, 211, 212

[56] References Cited

U.S. PATENT DOCUMENTS

| | | | |
|---|---|---|---|
| 4,711,541 | 12/1987 | Yoshino et al. | 351/214 |
| 4,884,880 | 12/1989 | Lichtman et al. | 359/368 |
| 4,927,254 | 5/1990 | Kino et al. | 359/368 |
| 5,020,891 | 6/1991 | Lichtman et al. | 359/235 |
| 5,099,354 | 3/1992 | Lichtman et al. | 359/389 |
| 5,235,457 | 8/1993 | Lichtman et al. | 359/368 |
| 5,321,446 | 6/1994 | Massig et al. | 351/214 |
| 5,410,376 | 4/1995 | Cornsweet et al. | 351/210 |

*Primary Examiner*—Thong Nguyen
*Assistant Examiner*—Mark Robinson
*Attorney, Agent, or Firm*—Rossi & Associates

[57] ABSTRACT

A slit lamp microscope, which includes an illumination optical system for slit illumination onto an eye to be examined and an observing optical system containing an objective lens for observation of the eye exposed to the slit illumination, comprises a confocal scanning microscope unit containing an illumination optical system for illuminating a rotating circular disc provided with a plurality of pinholes and illuminating an observation plane of the eye to be examined by illumination light transmitted through the pinholes of the rotating circular disc, and a light delivery optical system for focusing the luminous flux reflected from the observation plane of the eye on the rotating circular disc and delivering it to the objective lens, and a setting device to set the confocal scanning microscope unit in the front of the objective lens.

13 Claims, 6 Drawing Sheets

SLIT LAMP MICROSCOPE PROVIDED WITH A CONFOCAL SCANNING MECHANISM

BACKGROUND OF THE INVENTION

1. Field of the Invention

The present invention relates to slit lamp microscopes generally used for the observation of eyes to be examined and more particularly to a slit lamp microscope capable of confocal scanning microscopic observation.

2. Description of Related Art

Slit lamp microscopes have been widely used in ophthalmology, which project a slit light onto an eye to be examined and allow an examiner to observe a magnified object part of the eye illuminated by the slit light with a binocular stereoscopic microscope. In a case of the observation of the eye having opacity in its intermediate transparent body with conventional slit lamp microscopes, the slit light projected into the eye is scattered and reflected by the opacity, and thus it is flared, then it is difficult to obtain clear images of the object part of the eye.

A microscope capable of eliminating the scattered light to obtain clear images has been described in U.S. Pat. Nos. 4,884,880 and 4,927,254 respectively, which is known as the Kino microscope.

Further, it has been proposed a slit lamp microscope which is equipped, inside of a head part thereof, with a confocal scanning optical system of the Kino microscope. In detail, the head part of the slit lamp microscope is remodeled and a confocal scanning optical unit is inserted between an objective lens and binocular oculars of the slit lamp microscope.

However, there is a defect that the above confocal scanning unit can not be set in existent slit lamp microscopes as they are due to the necessity of remodeling the head part of the microscopes.

It is also difficult for the above slit lamp microscope to provide high magnifications because it is provided with a confocal scanning unit between an objective lens and binocular oculars. A slit lamp microscope thus having low magnifications can not produce only low contrast up efficiency on the image under observation. This results in that advantages of confocal observation are remarkably reduced.

SUMMARY OF THE INVENTION

The present invention has been made in view of the above circumstances and has an object to overcome the above problems and to provide a slit lamp microscope capable of generating confocal scanning images of a high magnification without largely remodeling the slit lamp microscope.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a slit lamp microscope of this invention includes an illumination optical system for slit illumination onto an eye to be examined and an observing optical system containing an objective lens for observation of the eye exposed to the slit illumination, the slit lamp microscope comprising a confocal scanning microscope unit containing an illumination optical system for illuminating a rotating circular disc provided with a plurality of pinholes and illuminating an observation plane of the eye to be examined by illumination light transmitted through the pinholes of the rotating circular disc, and a light delivery optical system for focusing the luminous flux reflected from the observation plane of the eye on the rotating circular disc and delivering it to the objective lens; and means for setting the confocal scanning microscope unit in the front of the objective lens.

According to the present invention, the slit lamp microscope can be easily used as a confocal scanning microscope without remodeling conventional slit lamp microscopes.

The confocal scanning microscope unit in the present invention can be displaced partially from the slit lamp microscope, and thus this will not spoil the observing function of the slit lamp microscope.

The confocal scanning microscope unit according to the present invention contains an objective lens used for only confocal scanning observation, so that the exchange of the objective lens for another one of higher magnification can easily effect producing confocal scanning observation images of a desired high magnification.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIGS. 8(a) and (b) are explanatory views of the sliding system to slide a unit slidable part of the confocal scanning microscope unit with respect to a unit fixed part, FIG. 6(a) being a plan view and FIG. 6(b) being a side view.

DETAILED DESCRIPTION OF THE PREFERRED EMBODIMENTS

A detailed description of a preferred embodiment of a slit lamp microscope embodying the present invention will now be given referring to the accompanying drawings.

Figure 1:
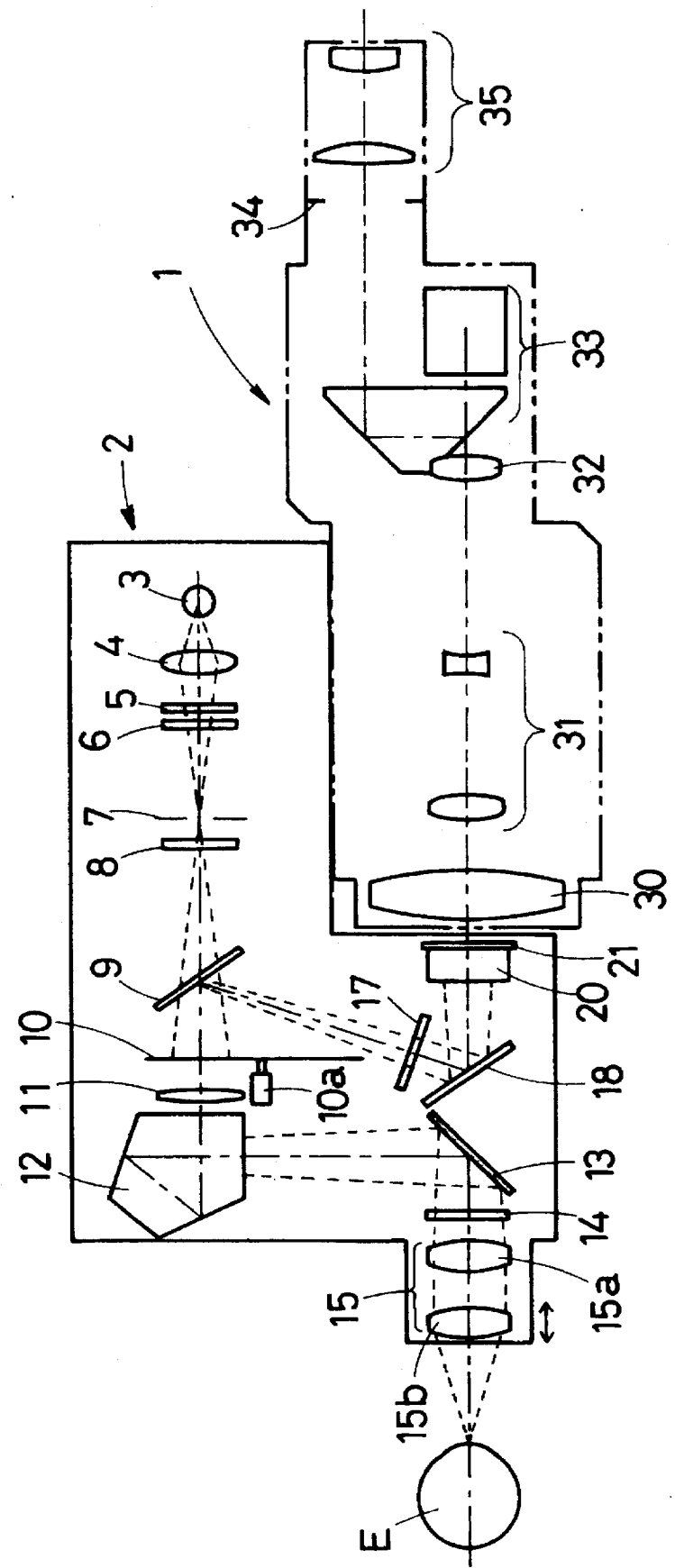
FIG. 1 is a schematic diagram of the optical systems of the apparatus in an embodiment according to the present invention, which is viewed from a side thereof when a confocal scanning microscope unit is mounted on a body of a slit lamp microscope.
Figure 2:
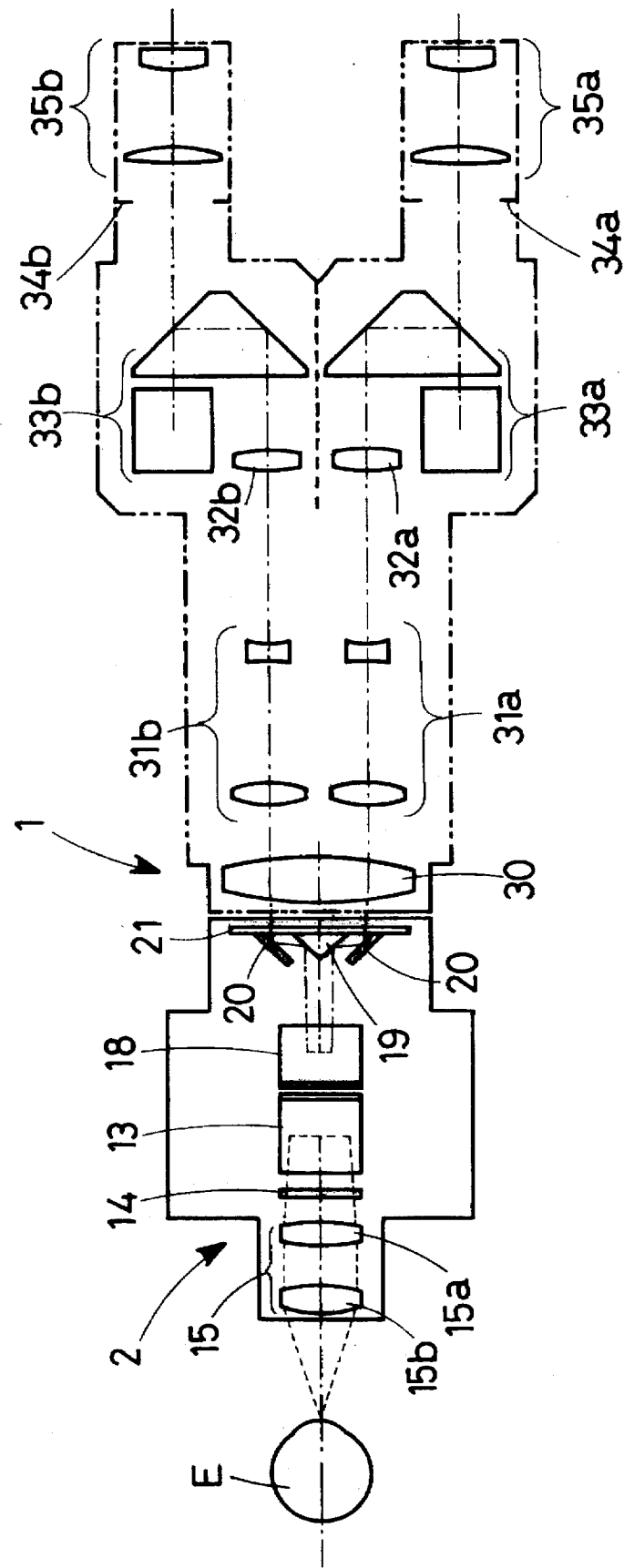
FIG. 2 is a plan view of the optical systems of FIG. 1.

FIG. 1 is a schematic diagram of optical systems of the apparatus in the present embodiment, the optical systems being in a condition that a slit lamp microscope body 1 is equipped with a confocal scanning microscope unit 2. FIG. 2 is the optical systems of FIG. 1, being viewed from above.

Figure 3:
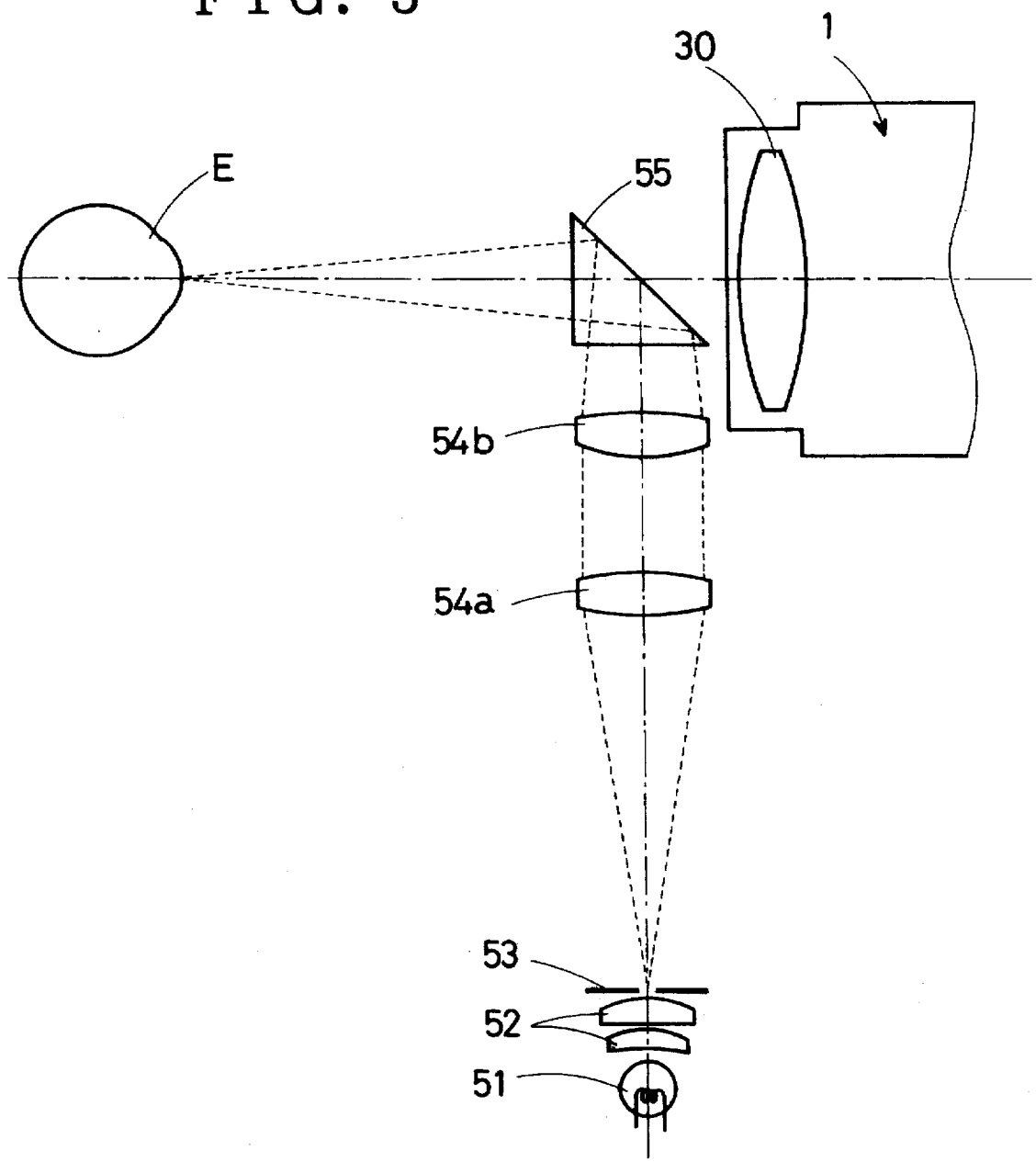
FIG. 3 is a schematic diagram of a slit illumination optical system.

The slit lamp microscope includes a slit illumination optical system to project a slit light onto an eye to be examined, the constitution of which is shown in FIG. 3. This slit illumination optical system is constituted of a light source 51 for slit illumination, a condenser lens 52, a slit 53, projection lenses 54a and 54b and a triangle prism 55, which is rotatable with respect to the slit lamp microscope body 1.

When the light source lamp 51 is turned on, a light therefrom is transmitted through the condenser lens 52 and the slit 53. The light passed through the slit 53 is then incident via the projection lenses 54a and 54b into the triangle prism 55 disposed on the optical axis of the slit lamp microscope body 1 including the objective lens 30, and deflected by the reflection plane of the prism 55 toward the eye E. The light is projected to the anterior parts of the eye E to form an image of the slit thereon. The light of a slit image reflected from the anterior parts of the eye E is incident into the slit lamp microscope body 1. At the time of the confocal scanning observation, the slit illumination optical system is turned and placed at such a position that will not obstruct the optical path for confocal scanning observation.

(Confocal Scanning Microscope Unit)

As shown in FIG. 1, the confocal scanning microscope unit 2 contains an illumination light source 3, a condenser lens 4, a filter 5 serving for interrupting an ultraviolet ray which is harmful to eyes, a filter 8 serving for interrupting an infrared light which is harmful to eyes, a diaphragm 7, a polarizer 8 which transforms the illumination light from the light source 3 into a linearly polarized light, and a beam-splitter 9. The components between the light source 3 and the polarizer 8 constitute an optical system belonging only to the illumination system. The beam-splitter 9 couples the illumination system and the observing system.

Numeral 10 is a rotating circular disc having a plurality of pinholes arranged spirally about a rotating axis of the circular disc 10, what is called a Nipkow disc. This circular disc 10 is positioned at a focus point of the object side in the slit lamp microscope body 1 and is rotatable at high speed by a motor 10a.

In the confocal scanning microscope unit 2, also provided are a field lens 11, a pentaprism 12 through which an image of light incident therein will be reversed, a mirror 13 for deflecting the optical path, a λ/4 plate (a quarterwave plate) 14 for transforming the illumination light which is linearly polarized light because of the transmission through the polarizer 8 into a circular polarized light and reversely a circular polarized light into a linearly polarized light. Numeral 15 is an objective lens group, constituted of a fixed lens 15a and a movable lens 15b which can be moved along the optical axis, which produce a substantially conjugate relationship between the rotating circular disc 10 and the observation plane of the eye to be examined. By moving the movable lens 15b, the fine focus adjustment can be achieved.

Numeral 17 is an analyzer arranged so that its polarizing axis is perpendicular to the polarizing axis of the polarizer 8.

The circular polarized light reflected on the observation plane of the eye E is transformed into a linearly polarized light through the quaterwave plate 14. This linearly polarized light has the direction turned by 90° from that of the illumination light, and consequently can transmits through the analyzer 17. Reflected lights from the surfaces of the rotating circular disc 10, the field lens 11 and the pentaprism 12 or the like are completely interrupted by the analyzer 17. Numeral 18 is a mirror for deflecting a light path for observation.

The light deflected by the mirror 18 is divided into two light beams via light beam dividing mirrors 19 and 20. This enables the examiner to observe the observation plane of the eye E as a stereo-image with the slit lamp microscope body 1. The two light beam dividing mirrors 20 are movable in a lateral direction in figures by means of adjusting a knob (not shown).

The movement of the light beam dividing mirrors 20 in relation to the mirror 19 will effect the change of the solid angle of two light beams. The examiner who observes the eye E with the slit lamp microscope body 1 can accordingly adjust the knob to change a stereoscopic effect of the image of the eye E. Numeral 21 is a window glass.

(Slit Lamp Microscope Body)

The slit lamp microscope body 1 is mainly constituted of an objective lens 30, variable power lenses 31a and 31b arranged behind the objective lens 30, image forming lenses 32a and 32b, erect prisms 33a and 33b, field stops 34a and 34b and oculars 35a and 35b, all systems except for the objective lens 30 being arranged as shown in FIG. 2 separately on two optical paths for binocular stereoscopic observation. The observer can observe an intermediate image formed on the field stops 34a and 34b through the oculars 35a and 35b.

Figure 4:
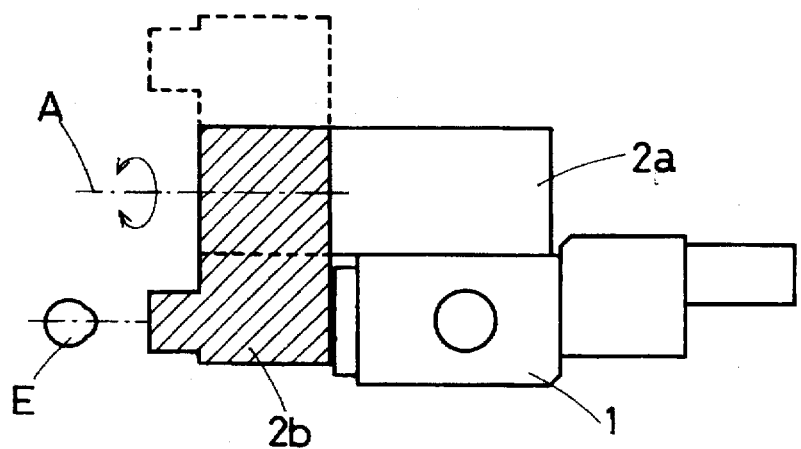
FIGS. 4(a) to (c) are schematic diagrams to show how to move a confocal scanning microscope unit into or out of the optical path of a slit lamp microscope.
Figure 4:
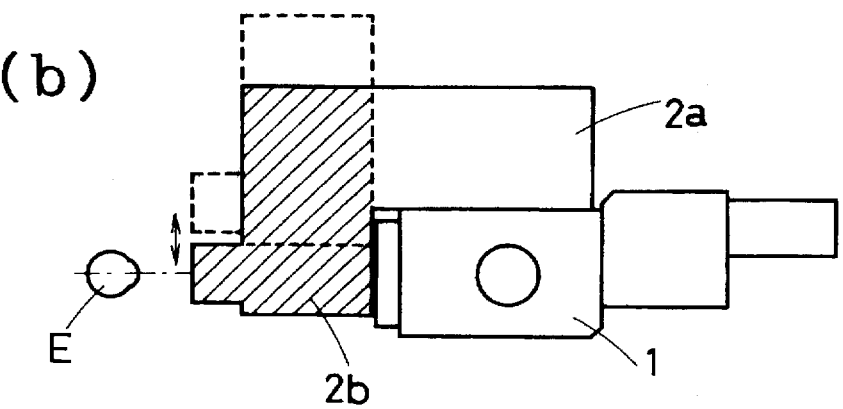
Figure 4:
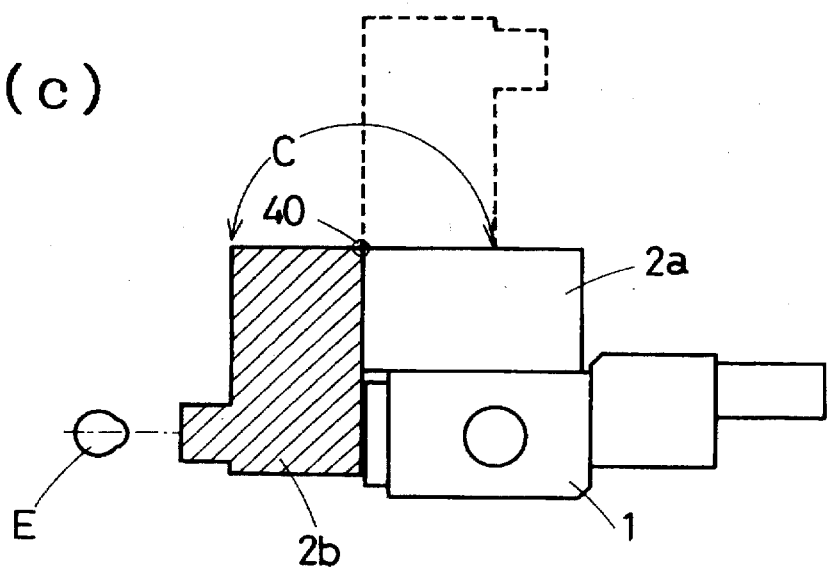

Next, FIGS. 4(a) to 4(c) show three embodiments of how to move the confocal scanning microscope unit 2 into or out of the optical path of the slit lamp microscope body 1.

Figure 5:
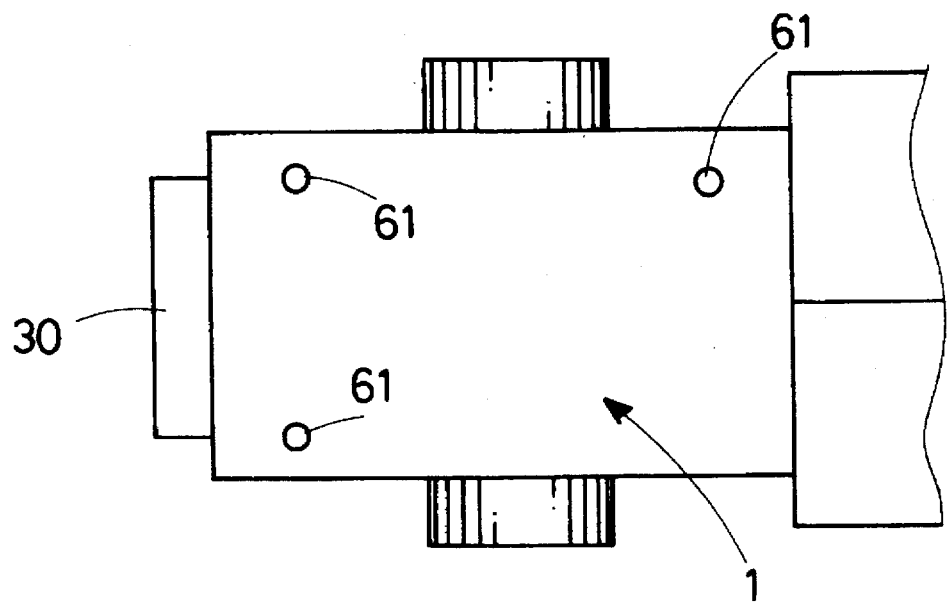
FIGS. 5(a) and (b) are explanatory views of a setting construction of the confocal scanning microscope unit on the slit lamp microscope body, FIG. 5(a) being a plan view and FIG. 5(b) being a side view.
Figure 5:
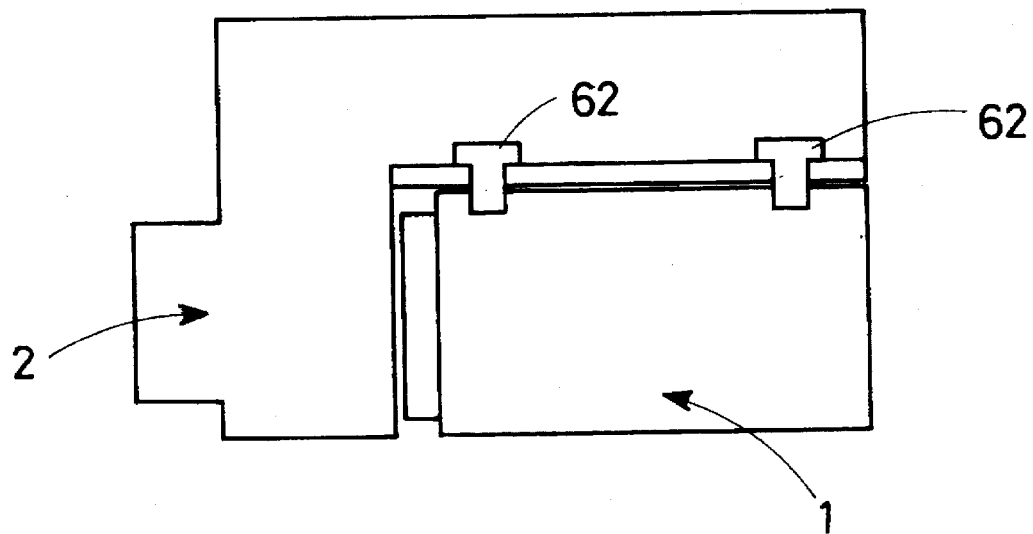

In FIG. 4(a), first, the confocal scanning microscope unit 2 is fixedly mounted, by its rear portion 2a, on a lens-barrel of the slit lamp microscope body 1. This mounting construction itself does not need any special mechanism. An embodiment thereof is shown in FIGS. 5(a) and 5(b). The slit lamp microscope body 1 is provided on its upper surface with several tapped holes 81, and the confocal scanning microscope unit 2 is secured on the slit lamp microscope body 1 with several mounting screws 82 fastened in the holes 81. Returning to FIG. 4(a), the forward portion 2b of the confocal scanning microscope unit 2 is pivotable about the rotation axis indicated by A with respect to the rear portion 2a, and comes to stop at a predetermined position by a click mechanism. The forward portion 2b is positioned at a position indicated by a dotted line at the time of slit lamp microscope observation, this makes it possible to ensure the optical path between the front surface of the objective lens 30 and the eye E to be examined.

Figure 6:
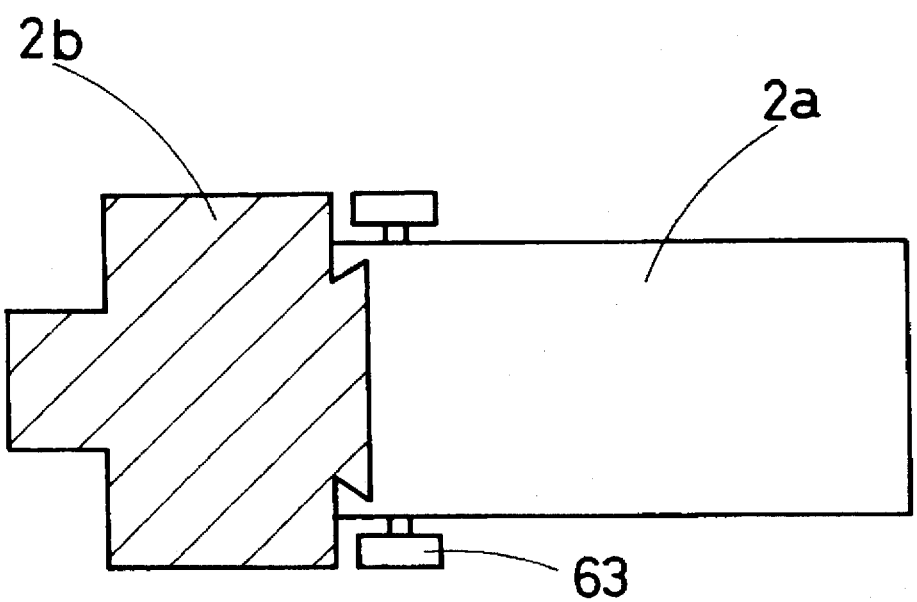
Figure 6:
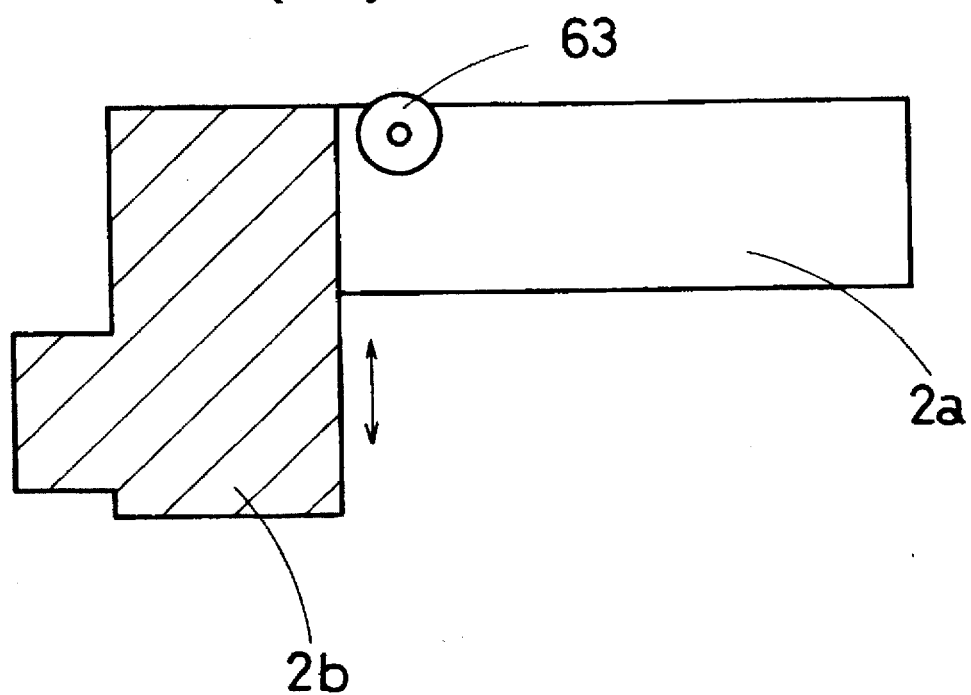

FIG. 4(b) shows a second embodiment in which the forward portion 2b is slidable vertically with respect to the rear portion 2a. In detail, as shown in FIGS. 6(a) and 6(b), the slide connecting portion between the slidable portion (forward portion) 2b and the fixed portion (rear portion) 2a is formed as dovetail groove construction, whereby the slidable portion 2b can be slid vertically. This sliding motion of the slidable portion 2b is adjusted via rack and pinion gear (not shown) by rotation of a knob 63.

FIG. 4(c) shows a third embodiment in which the forward portion 2b is pivotable about an axis 40 as indicated by an arrow C to a position indicated by a dotted line.

Observing operation with the apparatus constructed above will be described hereinafter.

After moving the slit illumination system out of the optical path of objective lens 30, the confocal scanning microscope unit 2 is set on a proper position for confocal scanning microscopic observation.

When the power supply of the unit 2 is charged, the illumination light source 3 is turned on and the motor 10a is driven to rotate the rotating circular disc 10 at high speed. Light emerged from the illumination light source 3 is condensed by the condenser lens 4 to converge on the diaphragm 7 via the ultraviolet ray interrupting filter 5 and the infrared ray interrupting filter 8. The light beam leaving from the diaphragm 7 is transformed into a linearly polarized light beam by the polarizer 8 and passed through the beam splitter 9 to illuminate the rotating circular disc 10. Luminous flux traveled through the pinholes of the rotating circular disc 10 is transmitted through the field lens 11 and the pentaprism 12, and deflected by the mirror 13. The linearly polarized light reflected by the mirror 13 is passed through the quaterwave plate 14 and there transformed into a circular polarized light. After that, the light passed through the objective lense groups 15 falls on the observation plane of the eye E, where it forms a number of pinhole images.

The circular polarized light scattered by the observation plane of the eye E is passed back through the quaterwave plate 14 and thus transformed into a linearly polarized light, whose direction of polarization being turned by an angle of 90° from that of the illumination light. This linearly polarized light is then deflected upward by the mirror 13, passed through the pentaprism 12 and the field lens 11, and imaged on the rotating circular disc 10 so that it can transmit through the pinholes of the rotating circular disc 10.

The light traveled through the pinholes of the circular disc 10 is reflected by the beam-splitter 9 and reaches the analyzer 17. The analyzer 17, being arranged so as to have the direction of polarization perpendicular to that of the polarizer 8, therefore blocks the reflection light from the circular disc 10, the field lens 11 and the pentaprism 12 or the like, and allows the light scattered by the observation plane of the eye E to pass therethrough.

The light passed through the analyzer 17 is then reflected by the mirror 18 and divided into two light beams by the light dividing mirrors 19 and 20. The two light beams transmits through the window glass 21 toward the objective lens 30 of the slit lamp microscope body 1. The examiner thus observes a stereoscopic intermediate image produced through the optical system of the slit lamp microscope body 1. At this time, only the reflection light from the illuminated region of the observation plane of the eye E by the light of the pinholes of the rotating circular disc 10 is transmitted back through the pinholes and reaches the examiner's eyes. The light can scan the entire observation plane of the eye E because the rotating circular disc 10 is provided thereon with a number of pinholes in spirals and rotated at high speed by motion of the motor 10a. The examiner can therefore observe the entire plane of the eye E. It is preferably to rotate the rotating circular disc 10 at a rotary speed whereat the examiner does not feel flicker due to scanning light.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A slit lamp microscope provided with a confocal scanning mechanism, which includes an illumination optical system for slit illumination onto an eye to be examined and an observing optical system containing an objective lens for observation of the eye exposed to the slit illumination, the slit lamp microscope comprising:

a confocal scanning microscope unit containing an illumination optical system for illuminating a rotating circular disc provided with a plurality of pinholes and illuminating an observation plane of the eye to be examined by illumination light transmitted through the pinholes of the rotating circular disc, and a light delivery optical system for focusing the luminous flux reflected from the observation plane of the eye on said rotating circular disc and delivering it to said objective lens; and means for locating said confocal scanning microscope unit in the front of said objective lens.

2. A slit lamp microscope provided with a confocal scanning mechanism according to claim 1, wherein said locating means comprises a locating system to move said confocal scanning microscope unit into or out of the optical path of an observation light, so that the direct observation of the eye to be examined is possible through the objective lens when said confocal scanning microscope unit is moved out of the observation optical path.

3. A slit lamp microscope provided with a confocal scanning mechanism according to claim 2, wherein said locating system includes means for rotating said confocal scanning microscope unit about an axis lying at a position apart from the observation optical path.

4. A slit lamp microscope provided with a confocal scanning mechanism according to claim 2, wherein said locating system includes means for sliding said confocal scanning microscope unit in the direction perpendicular to the observation optical path.

5. A slit lamp microscope provided with a confocal scanning mechanism according to claim 2, wherein said locating system includes means for pivoting said confocal scanning microscope unit within a plane including the observation optical path.

6. A slit lamp microscope provided with a confocal scanning mechanism according to claim 1, wherein said light delivery optical system comprises means for dividing luminous flux into two light beams, arranged behind said rotating circular disc.

7. A slit lamp microscope provided with a confocal scanning mechanism according to claim 6, wherein said luminous flux dividing means is constituted of a plurality of mirrors, the change of the positional relation between said mirrors causing the change of a solid angle.

8. A slit lamp microscope provided with a confocal scanning mechanism, said slit lamp microscope comprising:

a slit lamp microscope unit including a slit illumination optical system for projecting a light for slit illumination on an eye to be examined and an observing optical system for observing the eye illuminated by the slit illumination light;

a scanning microscope unit including a confocal scanning optical system for projecting a light for confocal scan on the eye to be examined and a rotating circular disc provided with a number of pinholes, said rotating circular disc being arranged in said confocal scanning optical system;

wherein, in confocal scanning on the eye to be examined, a light passed through the pinholes of the rotating circular disc being projected on the eye via the illumination optical system for confocal scan, and the reflection light from the eye being passed back through the pinholes and directed to the observing optical system of the slit lamp microscope unit; and wherein said confocal scanning microscope unit is arranged movably into or out of the optical path of said slit lamp microscope unit, so that the direct observation of the eye is possible through said observing optical system when said confocal scanning microscope unit is out of the observation optical path.

9. A slit lamp microscope provided with a confocal scanning mechanism according to claim 8, wherein said confocal scanning microscope unit is set in said slit lamp microscope unit so as to be rotatable in a plane perpendicular to the observation optical path about a rotation axis lying at a position apart from the optical path of the observation optical system.

10. A slit lamp microscope provided with a confocal scanning mechanism according to claim 8, wherein said confocal scanning microscope unit is set in said slit lamp microscope unit so as to be slidable in a direction vertically perpendicular to the observation optical path of the observing optical system.

11. A slit lamp microscope provided with a confocal scanning mechanism according to claim 8, wherein said confocal scanning microscope unit is set in said slit lamp microscope unit so as to be pivotable in a plane including the observation optical path about a rotation axis lying at a position apart from the optical path of said observing optical system.

12. A slit lamp microscope provided with a confocal scanning mechanism according to claim 8, wherein said observing optical system containing means for dividing luminous flux into two light beams behind said rotating circular disc.

13. A slit lamp microscope provided with a confocal scanning mechanism according to claim 12, wherein said luminous flux dividing means is constituted of a plurality of mirrors, the change of the positional relation between said mirrors causing the change of solid angle.

* * * * *